United States Patent
Yamamoto et al.

(10) Patent No.: US 9,943,220 B2
(45) Date of Patent: Apr. 17, 2018

(54) TUBULAR INSERTION SYSTEM

(71) Applicants: OLYMPUS MEDICAL SYSTEMS CORP., Tokyo (JP); OLYMPUS CORPORATION, Tokyo (JP)

(72) Inventors: Eiji Yamamoto, Musashimurayama (JP); Jun Hane, Tokyo (JP); Hiromasa Fujita, Hachioji (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 13/903,247

(22) Filed: May 28, 2013

(65) Prior Publication Data

US 2013/0261392 A1 Oct. 3, 2013

Related U.S. Application Data

(63) Continuation of application No. PCT/JP2011/077693, filed on Nov. 30, 2011.

(30) Foreign Application Priority Data

Dec. 1, 2010 (JP) .................................. 2010-268586

(51) Int. Cl.
*A61B 1/06* (2006.01)
*A61B 1/04* (2006.01)
(Continued)

(52) U.S. Cl.
CPC ........ *A61B 1/0051* (2013.01); *A61B 1/00006* (2013.01); *A61B 1/0052* (2013.01);
(Continued)

(58) Field of Classification Search
CPC ........... A61B 5/06; A61B 5/061–5/068; A61B 19/5244; A61B 2019/5246;
(Continued)

(56) References Cited

U.S. PATENT DOCUMENTS 6,371,907 B1 4/2002 Hasegawa et al.
7,331,924 B2 2/2008 Arai et al.
(Continued)

FOREIGN PATENT DOCUMENTS

JP 3-198828 A 8/1991
JP 6-154153 A 6/1994
(Continued)

OTHER PUBLICATIONS

Japanese Office Action dated Dec. 2, 2014 received from related Application No. 2010-268586, together with an English-language translation.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A tubular insertion system includes an insertion unit including a bendable portion, a bending operation mechanism that operates the bendable portion. The tubular insertion system further includes a bending operation amount detection/calculation device that calculates bending operation amount information, a bent shape detection/calculation device that calculates bent shape information, and a first operation support information acquisition unit that acquires first operation support information based on at least one of the bending operation amount information and the bent shape information.

8 Claims, 8 Drawing Sheets

(51) Int. Cl.
*A61B 1/00* (2006.01)
*A61B 1/005* (2006.01)
*G02B 23/24* (2006.01)
*A61B 17/00* (2006.01)
*A61B 34/20* (2016.01)

(52) U.S. Cl.
CPC ...... *G02B 23/2476* (2013.01); *A61B 1/00043* (2013.01); *A61B 2017/00327* (2013.01); *A61B 2034/2061* (2016.02)

(58) Field of Classification Search
CPC .... A61B 2019/5248; A61B 2019/5251; A61B 2019/5261; A61B 1/005; A61B 1/0051; A61B 1/0052; A61B 1/0055; A61B 1/0057; A61B 1/00147; A61B 1/00006
USPC ................................ 600/109, 139–152, 160
See application file for complete search history.

(56) References Cited

U.S. PATENT DOCUMENTS

| | | | |
|---|---|---|---|
| 2007/0112255 A1* | 5/2007 | Ikeda et al. ............. | A61B 1/00 600/146 |
| 2008/0221592 A1* | 9/2008 | Kawai ................... | A61B 19/00 606/130 |
| 2009/0149711 A1 | 6/2009 | Tanaka et al. | |
| 2010/0161129 A1* | 6/2010 | Costa ..................... | B25J 9/1697 700/259 |
| 2011/0234780 A1* | 9/2011 | Ito et al. ................ | H04N 7/18 348/65 |
| 2011/0282154 A1* | 11/2011 | Umemoto ............... | A61B 1/00 600/152 |
| 2013/0312563 A1* | 11/2013 | Kawashima ............ | B25J 18/02 74/490.01 |

FOREIGN PATENT DOCUMENTS

| | | |
|---|---|---|
| JP | 11-281897 A | 10/1999 |
| JP | 2001-169998 A | 6/2001 |
| JP | 2009-131406 | 6/2009 |
| JP | 2009-136618 | 6/2009 |
| JP | 2010-35768 | 2/2010 |

OTHER PUBLICATIONS

Extended Supplementary Search Report dated May 28, 2014 from related European Application No. 11 84 5575.7.
International Preliminary Report on Patentability together with the Written Opinion dated Jun. 13, 2013 received in related International Application No. PCT/JP2011/077693.
International Search Report dated Jan. 31, 2012 issued in PCT/JP2011/077693.
European Patent Office Communication dated Dec. 1, 2016 in corresponding European Application No. 11 845 575.7.

* cited by examiner

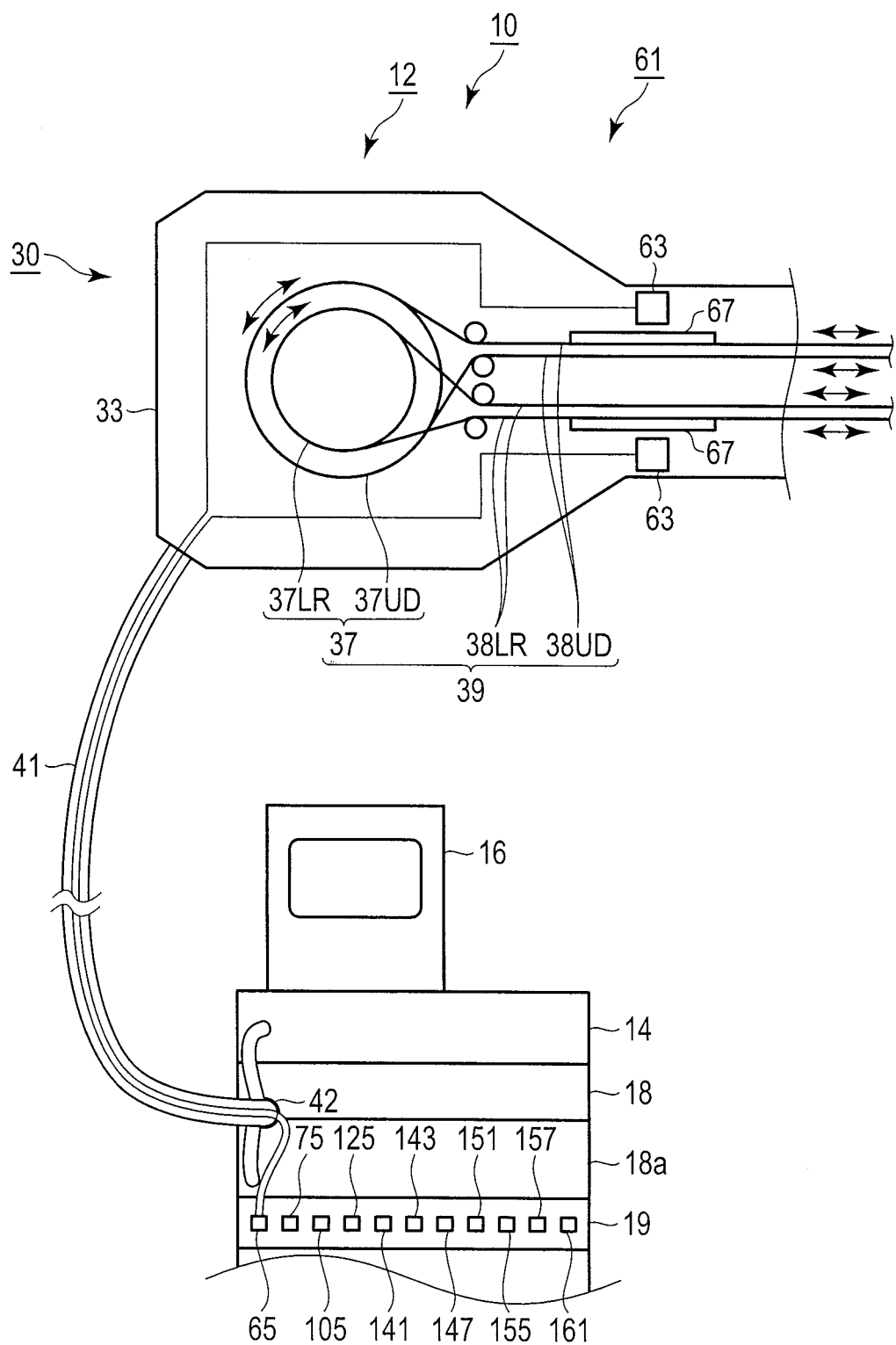
F I G. 2A

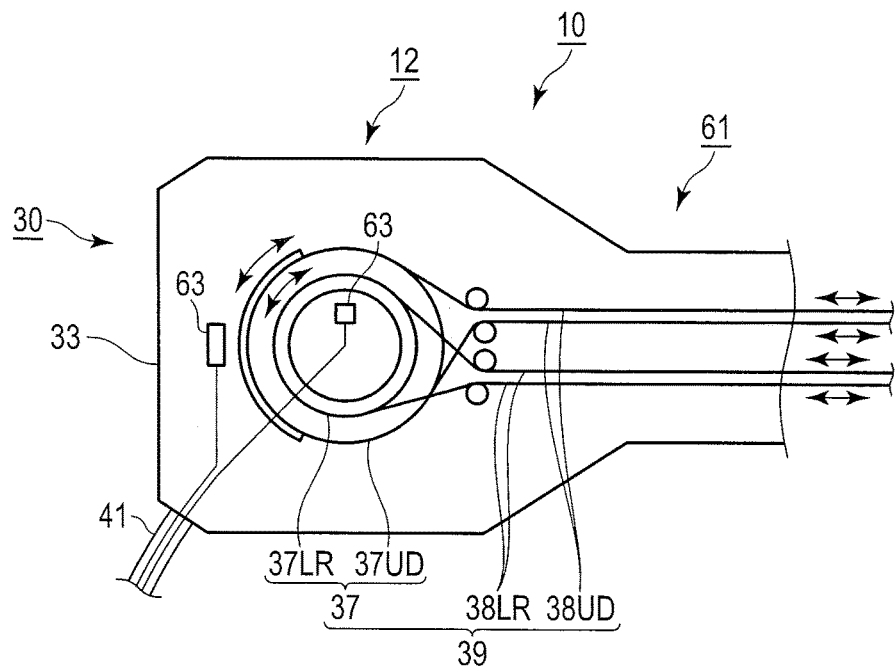
F I G. 2B
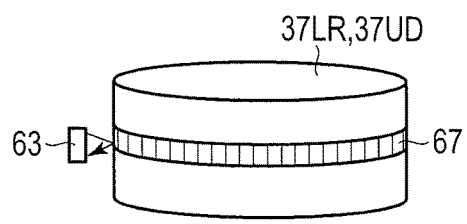
F I G. 2C
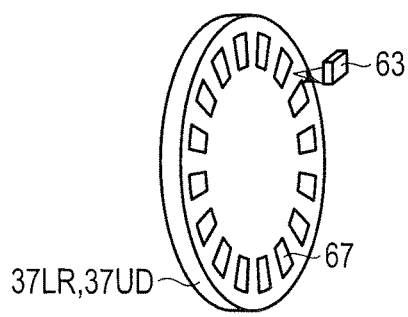
F I G. 2D

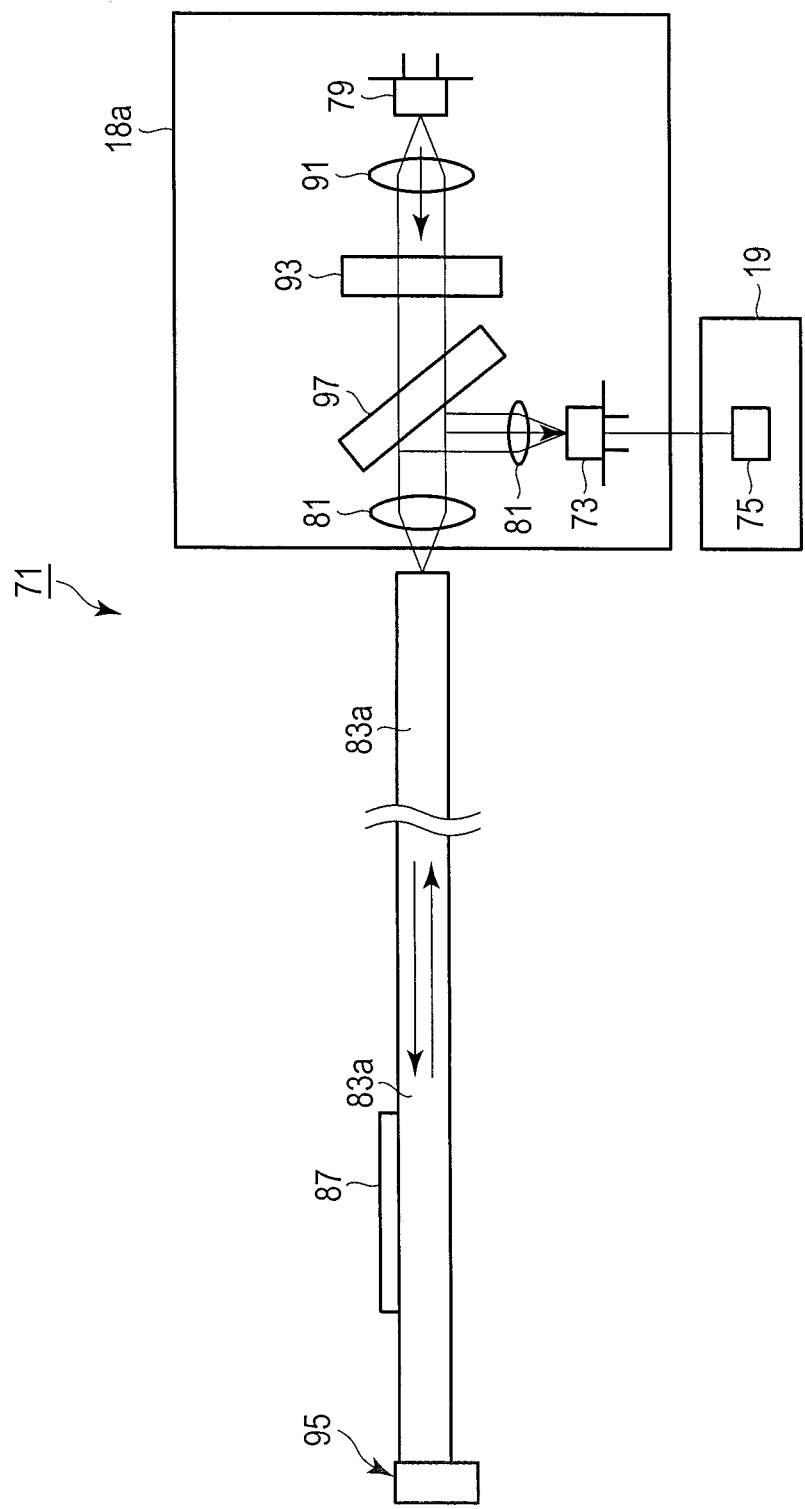
F I G. 3B

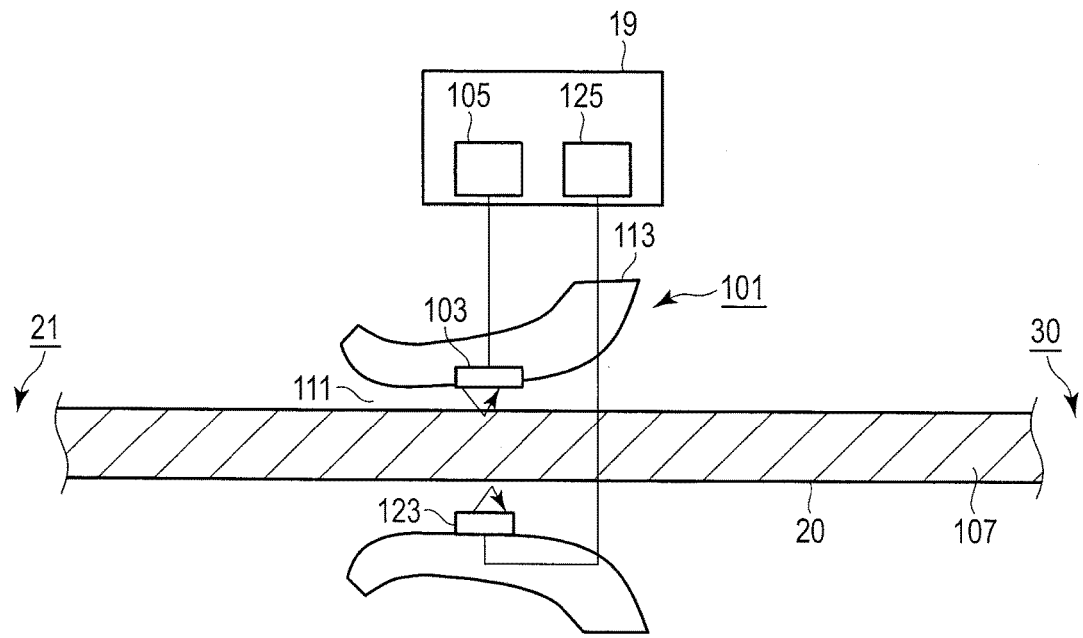
F I G. 4B
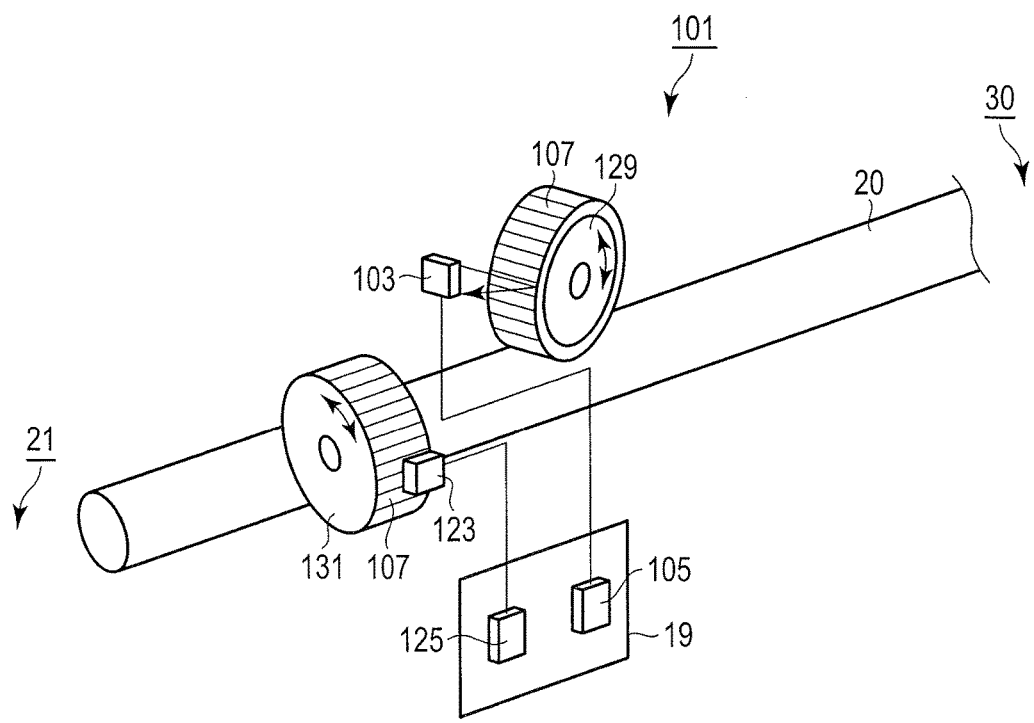
F I G. 4C

TUBULAR INSERTION SYSTEM

CROSS-REFERENCE TO RELATED APPLICATIONS

This application is a Continuation application of PCT Application No. PCT/JP2011/077693, filed Nov. 30, 2011 and based upon and claiming the benefit of priority from prior Japanese Patent Application No. 2010-268586, filed Dec. 1, 2010, the entire contents of all of which are incorporated herein by reference.

BACKGROUND OF THE INVENTION

1. Field of the Invention

The present invention relates to a tubular insertion system.

2. Description of the Related Art

An endoscope includes an insertion unit. In general, a distal end portion of the insertion unit includes a measuring unit for measuring capacity when the insertion unit is inserted. Such the measuring unit is, for example, a strain gauge (pressure-sensitive sensor).

Such an endoscope is disclosed by, for example, Jpn. Pat. Appln. KOKAI Publication No. H6-154153. In Jpn. Pat. Appln. KOKAI Publication No. H6-154153, a pressure sensitive sensor as a measuring unit is disposed in a distal end portion of an insertion unit of an endoscope, a catheter or the like. The pressure-sensitive sensor detects capacity (pressure-sensitive information). Detection results are useful for operation as operation support information indicating support of operation when the insertion unit is inserted and the insertion unit is bent. The operation includes an insertion operation of the insertion unit, a rotating operation of the insertion unit, and a bending operation of the insertion unit. The operation support information is very important when operating Jpn. Pat. Appln. KOKAI Publication No. H6-154153 described above, it is necessary for an operator to grasp pressure-sensitive information in the distal end portion indicating operation support information correctly with high precision so that the operator can easily insert the insertion unit.

It is also desirable for the operator to know operation support information such as shape information of the insertion unit other than the pressure-sensitive information so that the operator can easily insert the insertion unit. To acquire such operation support information (shape information of the insertion unit), the operator needs to correctly grasp pressure-sensitive information from all directions.

Thus, Jpn. Pat. Appln. KOKAI Publication No. H6-154153 described above, the pressure-sensitive sensors are suitably disposed like being distributed over the entire distal end portion of the insertion unit. However, it is not easy to dispose many pressure-sensitive sensors in such a manner due to an increasingly thin distal end portion and in terms of limited wiring space in the insertion unit. Moreover, performance of the pressure-sensitive sensor is greatly affected by noise and the arrangement position of the pressure-sensitive sensor.

It is still more difficult to build a sensing system that simultaneously detects various kinds of operation support information.

Thus, there is a possibility that operation support information cannot be acquired easily with high precision.

BRIEF SUMMARY OF THE INVENTION

The present invention is made in view of the above circumstances and an object thereof is to provide a tubular insertion system capable of acquiring operation support information easily with high precision.

According to an aspect of embodiments, a tubular insertion system includes an insertion unit comprising a bendable portion that is bent, a bending operation mechanism that operates the bendable portion to bend the bendable portion, a bending operation amount detection/calculation device that detects an operation of the bending operation mechanism to calculation bending operation amount information indicating an amount of the operation, a bent shape detection/calculation device that detects a bent shape of the bendable portion to calculate bent shape information indicating the bent shape, and a first operation support information acquisition unit that acquires first operation support information indicating support of the operation of the bendable portion based on at least one of the bending operation amount information and the bent shape information.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a diagram illustrating a bending operation amount detection/calculation device.

FIG. 2B is a diagram illustrating the bending operation amount detection/calculation device.

FIG. 2C is a diagram illustrating a relationship between a read portion and a bending operation amount detection unit which are disposed in a bending operation unit.

FIG. 2D is a diagram illustrating the relationship between the read portion and the bending operation amount detection unit which are disposed in the bending operation unit.

FIG. 3B is a diagram illustrating the bent shape detection/calculation device.

FIG. 4B is a diagram illustrating an insertion/removal and rotating operation detection/calculation device.

FIG. 4C is a diagram illustrating the insertion/removal and rotating operation detection/calculation device.

DETAILED DESCRIPTION OF THE INVENTION

An embodiment of the present invention will be described below with reference to drawings.

A first embodiment will be described with reference to FIGS. 1, 2A, 2B, 2C, 2D, 3A, 3B, 4A, 4B, 4C, and 5. For the simplification of illustration, a portion of members is omitted in some drawings.

Figure 1:
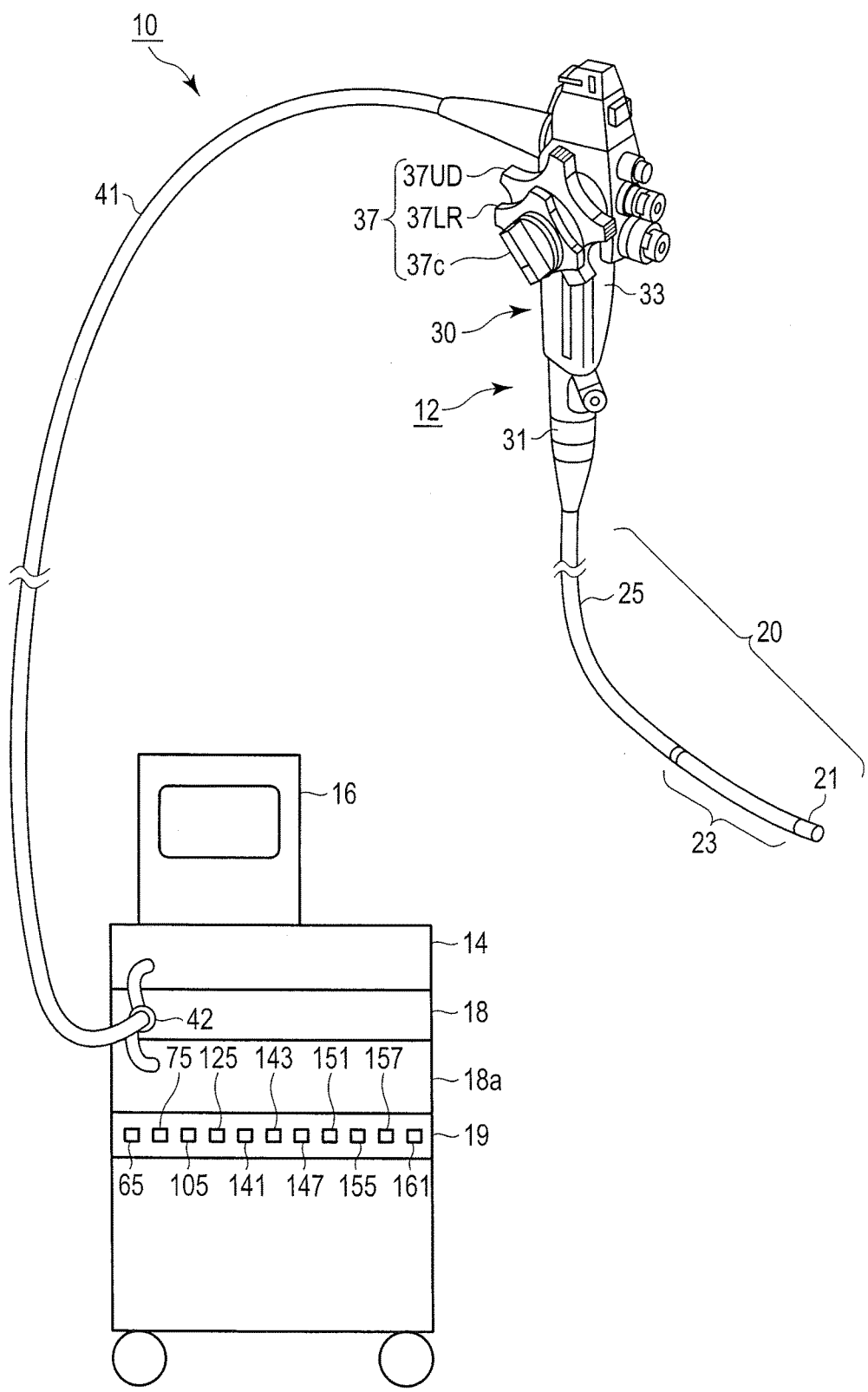
FIG. 1 is a schematic diagram of a tubular insertion system according to the present invention.

As shown in FIG. 1, an endoscope system (tubular insertion system) 10 includes, for example, an endoscope 12 that images a desired observation object, an image processing apparatus 14 (for example, a video processor) that performs image processing of the observation object imaged by the endoscope 12, and a monitor 16 as a display unit connected to the image processing apparatus 14 to display the observation object imaged by the endoscope 12 and processed by the image processing apparatus 14. The endoscope system 10 also includes a light source apparatus 18 that emits illumination light toward the endoscope 12, a light emission detection apparatus 18a that emits light different from the illumination light emitted from the light source apparatus 18 to detect the light, and a control apparatus 19 that controls the endoscope system 10 including the endoscope 12, the image processing apparatus 14, the monitor 16, the light source apparatus 18, and the light emission detection apparatus 18a.

The observation object is an affected area, lesion or the like inside a sample (for example, a body cavity [lumen]).

As shown in FIG. 1, the endoscope 12 includes a hollow elongated insertion unit 20 inserted into a body cavity of a patient and an operation unit 30 linked to a proximal end portion of the insertion unit 20 to operate the endoscope 12. The endoscope 12 is a tubular insertion apparatus that inserts the tubular insertion unit 20 into a body cavity.

The insertion unit 20 includes a distal end hard portion 21, a bendable portion 23 that is bent, and a flexible tubular portion 25 from a distal end portion side of the insertion unit 20 toward the proximal end portion side. A proximal end portion of the distal hard portion 21 is linked to a distal end portion of the bendable portion 23 and a proximal end portion of the bendable portion 23 is linked to a distal end portion of the flexible tubular portion 25.

The distal end hard portion 21 is the distal end portion of the insertion unit 20 and the distal end portion of the endoscope 12 and is hard.

The bendable portion 23 is bent in a desired direction like up and down, left and right by operating a bending operation unit 37 described later. The position and orientation of the distal end hard portion 21 are changed by the bendable portion 23 being bent so that an observation object comes within the range of observation and the observation object is illuminated with illumination light. The bendable portion 23 is configured by node rings (not shown) being rotationally movably linked each other along longitudinal axis directions of the insertion unit 20.

The flexible tubular portion 25 has desired flexibility and is bent by an external force. The flexible tubular portion 25 is a tubular member extending from a body portion 31 described later of the operation unit 30.

The operation unit 30 includes the body portion 31 from which the flexible tubular portion 25 extends, a grasping portion 33 linked to the proximal end portion of the body portion 31 and grasped by an operator who operates the endoscope 12, and a universal cord 41 connected to the grasping portion 33.

As shown in FIGS. 1 and 2A, the grasping portion 33 includes the bending operation unit 37 that operates operation wires 38LR, 38UD described later to bend the bendable portion 23. The bending operation unit 37 includes a left-right bending operation knob 37LR that performs a bending operation of the bendable portion 23 left and right, an up-down right bending operation knob 37UD that performs a bending operation of the bendable portion 23 up and down, and a fixing knob 37c that fixes the position of the bendable portion 23 that is bent.

The left-right bending operation knob 37LR is connected to a bending operation drive unit (not shown) in the left and right direction driven by the left-right bending operation knob 37LR. The up-down bending operation knob 37UD is connected to a bending operation drive unit (not shown) in the up and down direction driven by the left-right bending operation knob 37UD. The bending operation drive unit in the up and down direction and the bending operation drive unit in the left and right direction are disposed, for example, inside the grasping portion 33.

The bending operation drive unit in the left and right direction is connected to the operation wire 38LR inserted through the operation unit 30, the flexible tubular portion 25, and the bendable portion 23. The operation wire 38LR is also connected to the distal end portion of the bendable portion 23.

The bending operation drive unit in the up and down direction is connected to the operation wire 38UD inserted through the operation unit 30, the flexible tubular portion 25, and the bendable portion 23. The operation wire 38UD is different from the operation wire 38LR. The operation wire 38UD is connected to the distal end portion of the bendable portion 23.

The left-right bending operation knob 37LR bends the bendable portion 23 in the left and right direction via the bending operation drive unit in the left and right direction and the operation wire 38LR. The up-down bending operation knob 37UD bends the bendable portion 23 in the up and down direction via the bending operation drive unit in the up and down direction and the operation wire 38UD.

The bending operation units 37 (the left-right bending operation knob 37LR and the up-down bending operation knob 37UD), the bending operation drive unit in the left and right direction, the operation wire 38LR, the bending operation drive unit in the up and down direction, and the operation wire 38UD function as a bending operation mechanism 39 that operates the bendable portion 23 to bend the bendable portion 23.

The universal cord 41 extends from the side face of the grasping portion 33. The universal cord 41 has a connector 42 at a proximal end portion thereof that can be attached/detached to/from the image processing apparatus 14, the light source apparatus 18, and the light emission detection apparatus 18a.

The image processing apparatus 14, the light source apparatus 18, the light emission detection apparatus 18a, and the control apparatus 19 are mutually connected. The image processing apparatus 14, the light source apparatus 18, and the light emission detection apparatus 18a are freely detachably connected to the endoscope 12 via the connector 42.

As shown in FIGS. 2A, 2B, 3A, 3B, and 5, the endoscope system 10 includes a bending operation amount detection/calculation device 61 that detects an operation of the bending operation mechanism 39 to calculate bending operation amount information indicating the amount of operation and a bent shape detection/calculation device 71 that detects the bent shape (curvature amount) of the bendable portion 23 that is actually bent to calculation bent shape information indicating the bent shape.

As shown in FIGS. 2A and 2B, the bending operation amount of the bending operation mechanism 39 in the bending operation amount detection/calculation device 61 indicates a bending operation amount by which the bending operation mechanism 39 is operated to bend the bendable portion 23. More specifically, the bending operation amount of the bending operation mechanism 39 indicates, as shown in FIG. 2A, a bending operation amount by which the operation wires 38LR, 38UD are operated or, as shown in FIG. 2B, a bending operation amount by which the bending operation unit 37 is operated.

The bending operation amount detection/calculation device 61 includes a bending operation amount detection unit 63 that detects the bending operation amount of the bending operation mechanism 39 and a bending operation amount calculation unit 65 that calculates bending operation amount information based on detection results by the bending operation amount detection unit 63.

As shown in FIG. 2A, a read portion 67, for example, a linear scale is disposed, for example, at a proximal end portion of the operation wire 38LR and at a proximal end portion of the operation wire 38UD for the bending operation amount detection unit 63 to detect the bending operation amount of the bending operation mechanism 39. The read portion 67 moves together with the operation wires 38LR, 38UD by the operation wires 38LR, 38UD being moved.

The bending operation amount detection unit 63 reads the read portion 67 moving together with the operation wires 38LR, 38UD to detect the movement of the read portion 67. Accordingly, the bending operation amount detection unit 63 detects the movement of the operation wires 38LR, 38UD. The bending operation amount detection unit 63 is, for example, a linear encoder and is disposed, for example, inside the operation unit 30.

The bending operation amount calculation unit 65 detects the amount of movement of the read portion 67, that is, the amount of movement of the operation wire 38LR and the operation wire 38UD based on operation results detected by the bending operation amount detection unit 63. Then, based on detection results, the bending operation amount calculation unit 65 operates bending operation amount information of the operation wire 38LR and the operation wire 38UD. The bending operation amount calculation unit 65 detects the bending operation amount of the bending operation mechanism 39 by calculating the bending operation amount information of the operation wire 38LR and the operation wire 38UD, resulting in the calculation of the bending operation amount information. As shown in FIGS. 1 and 2A, the bending operation amount calculation unit 65 is disposed, for example, in the control apparatus 19.

Thus, the bending operation amount detection/calculation device 61 detects the bending operation amount of the bending operation mechanism 39 based on the amount of movement of the operation wires 38LR, 38UD in the bending operation mechanism 39 to calculate bending operation amount information.

As shown in FIGS. 2B and 2C, the read portion 67 may be disposed in the left-right bending operation knob 37LR and the up-down bending operation knob 37UD. In this case, the read portion 67 is disposed, for example, on the outer circumferential surface of the left-right bending operation knob 37LR of the cylinder and the outer circumferential surface of the up-down bending operation knob 37UD of the cylinder.

Also as shown in FIGS. 2B and 2D, the read portion 67 may be disposed on the surface of the left-right bending operation knob 37LR and the surface of the up-down bending operation knob 37UD.

In these cases, the bending operation amount detection unit 63 reads the read portion 67 rotationally moving together with the left-right bending operation knob 37LR and the up-down bending operation knob 37UD to detect the rotation of the read portion 67. Accordingly, the bending operation amount detection unit 63 detects the rotational movement of the left-right bending operation knob 37LR and the up-down bending operation knob 37UD. The bending operation amount detection unit 63 is, for example, a rotary encoder.

The bending operation amount calculation unit 65 detects the amount of movement of the read portion 67, that is, the amount of rotational movement of the left-right bending operation knob 37LR and the up-down bending operation knob 37UD based on detection results detected by the bending operation amount detection unit 63. Then, based on detection results, the bending operation amount calculation unit 65 calculates bending operation amount information of the left-right bending operation knob 37LR and the up-down bending operation knob 37UD. The bending operation amount calculation unit 65 detects the bending operation amount of the bending operation mechanism 39 by calculating the bending operation amount information of the left-right bending operation knob 37LR and the up-down bending operation knob 37UD, resulting in the calculation of the bending operation amount information.

Thus, the bending operation amount detection/calculation device 61 detects the bending operation amount of the bending operation mechanism 39 based on the amount of rotational movement of the left-right bending operation knob 37LR and up-down bending operation knob 37UD in the bending operation mechanism 39 to calculate bending operation amount information.

Incidentally, the read portion 67 described above is included in the bending operation amount detection/calculation device 61.

In the present embodiment, as described above, the bendable portion 23 is bent up and down, left and right, but may be bent up and down only or left and right only. In such a case, the bending operation amount detection/calculation device 61 detects the bending operation amount in the up and down direction or the bending operation amount in the left and right direction of the bending operation mechanism 39 to calculate bending operation amount information of each.

Thus, the bending operation amount detection/calculation device 61 detects at least one of the bending operation amount in the up and down direction of the bending operation mechanism 39 when the bendable portion 23 is bent in the up and down direction and the bending operation amount in the left and right direction of the bending operation mechanism 39 when the bendable portion 23 is bent in the left and right direction to calculate bending operation amount information.

Figure 3A:
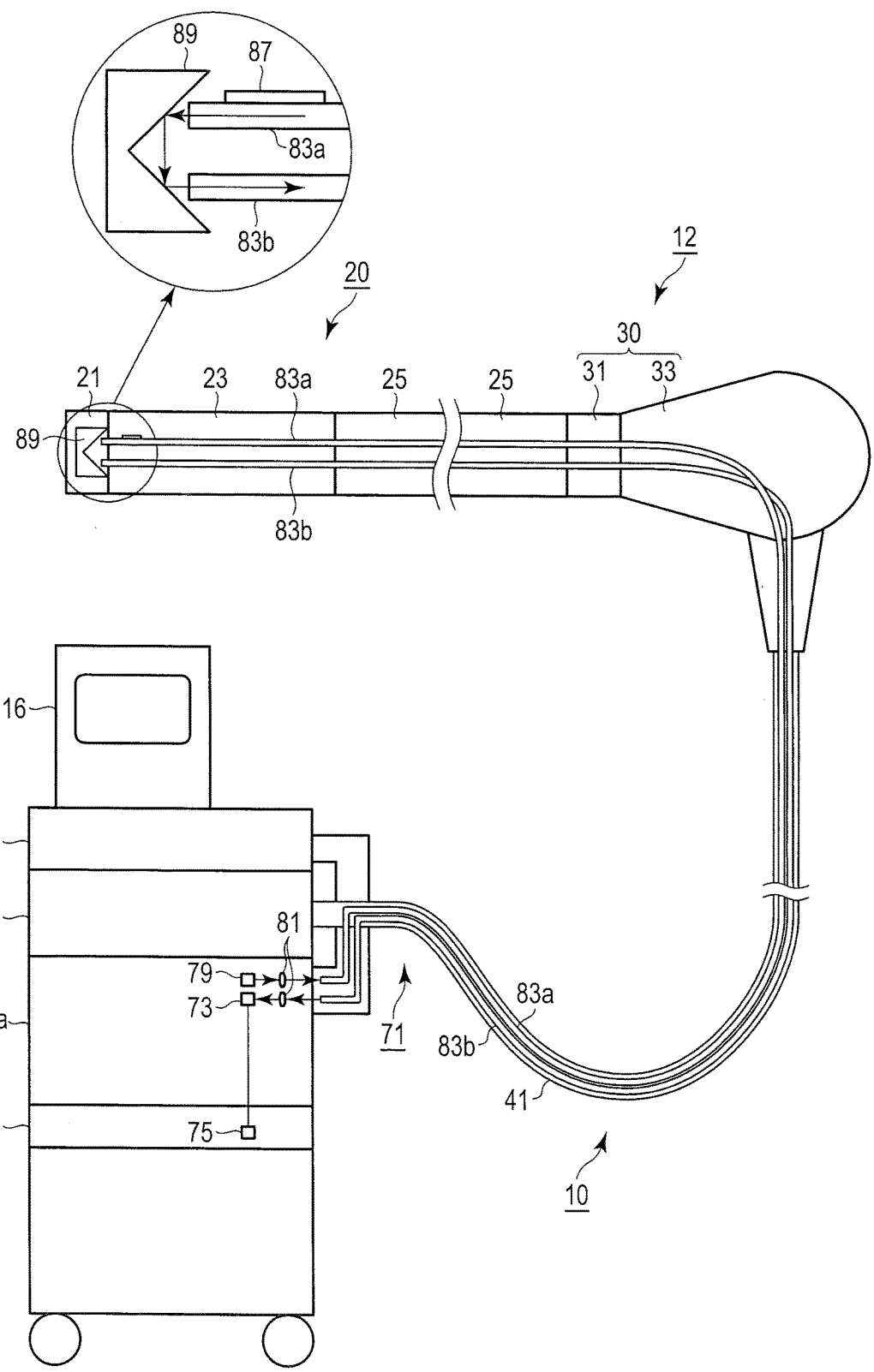
FIG. 3A is a diagram illustrating a bent shape detection/calculation device.

As shown in FIG. 3A, the bent shape detection/calculation device 71 includes the light emission detection apparatus 18a described above.

The light emission detection apparatus 18a includes a light source 79 that emits light, for example, an LED and a condenser lens 81 that condenses light emitted from the LED. The condenser lens 81 is disposed between the light source 79 and an optical fiber 83a described later and between an optical fiber 83b described later and a bent shape detection unit 73 described later. The condenser lens 81 condenses light to the optical fiber 83a so that the light emitted from the light source 79 enters the optical fiber 83a. Also, the condenser lens 81 condenses light guided (returned) by the optical fiber 83b from the distal end hard portion 21 to the light emission detection apparatus 18a to the bent shape detection unit 73.

The bent shape detection/calculation device 71 also includes a linear member that is disposed linearly along the longitudinal direction of the insertion unit 20, can be bent, and whose characteristics are changed by being bent, a bent shape detection unit 73 that detects the bent shape of the bendable portion 23 based on characteristics of the linear member when the linear member is bent accompanying the curvature of the bendable portion 23 and a bent shape calculation unit 75 that calculates the bent shape of the bendable portion 23 that is actually bent based on detection results of the bent shape detection unit 73.

The linear member indicates the optical fiber 83a that guides light emitted from the light source 79 and condensed by the condenser lens 81 to the distal end hard portion 21 via the operation unit 30 and the insertion unit 20 and the optical fiber 83b that guides light returning from the distal end hard portion 21 to the light emission detection apparatus 18a from the distal end hard portion 21 to the bent shape detection unit 73 via the insertion unit 20 and the operation unit 30.

The optical fiber 83a and the optical fiber 83b are inserted through the universal cord 41, the operation unit 30, and the insertion unit 20. The optical fiber 83a and the optical fiber 83b described above are light-guiding members capable of guiding light emitted from the light source 79 along the longitudinal direction of the insertion unit 20.

In the linear member, the optical fiber 83a includes at least one processed region 87 processed so that light is emitted (leaked) out of the optical fiber 83a when the bendable portion 23 is bent. The processed region 87 is an optical characteristics changing portion that changes optical characteristics (for example, the amount of light) of light guided by the optical fiber 83a in accordance with the bent state of the insertion unit 20. The processed region 87 is disposed near a location where the curvature of the insertion unit 20 should be detected, for example, in the bendable portion 23.

As shown in FIG. 3A, the distal end hard portion 21 includes a reflection portion 89 that reflects light in such a way that light emitted from the optical fiber 83a is caused to enter the optical fiber 83b so that the bent shape detection unit 73 can detect the bent shape of the bendable portion 23 based on characteristics of the linear member. The reflection portion 89 is, for example, a corner cube.

As shown in FIG. 3A, the bent shape detection unit 73 is disposed, for example, in the light emission detection apparatus 18a and, as shown in FIGS. 1 and 3A, the bent shape calculation unit 75 is disposed in the control apparatus 19. The bent shape detection unit 73 is a receiving unit like, for example, a light receiving element.

In the present embodiment, the optical fiber 83a in the bendable portion 23 is bent by the bendable portion 23 being bent and a portion of light is thereby emitted (leaked) to the outside through the processed region 87. That is, the processed region 87 as an optical characteristics changing portion changes optical characteristics (for example, the amount of light) of the optical fiber 83a. When the processed region 87 changes optical characteristics, the bent shape detection unit 73 detects the bent shape of the bendable portion 23, more specifically, the direction and size of the curvature based on the changed optical characteristics (for example, the amount of light).

The bent shape calculation unit 75 calculates the bent shape of the bendable portion 23 that is actually bent based on detection results by the bent shape detection unit 73.

Optical characteristics are not limited to, for example, the amount of light and may be, for example, the spectrum or a state of light such as polarization and the bent shape detection unit 73 only needs to be able to detect corresponding optical characteristics.

As shown in FIG. 3B, instead of the optical fiber 83b, a light projection lens 91, an isolator 93, the condenser lens 81, a reflection portion 95, and a reflection mirror 97 may be disposed. The light projection lens 91 projects light emitted from the light source 79. The condenser lens 81 condenses light to the optical fiber 83a so that the light having passed through the isolator 93 enters the optical fiber 83a. The reflection portion 95 is a mirror that reflects light so that the light emitted from the optical fiber 83a enters the optical fiber 83a. The reflection mirror 97 reflects light guided by the optical fiber 83a to return and emitted from the optical fiber 83a toward the bent shape detection unit 73.

The reflection portion 95 is disposed in the distal end hard portion 21 and the light projection lens 91, the isolator 93, the condenser lens 81, and the reflection lens 97 are disposed in the light emission detection apparatus 18a.

The light emission detection apparatus 18a, the light source 79, the condenser lens 81, the optical fibers 83a, 83b, the reflection portion 89, the light projection lens 91, the isolator 93, the reflection portion 95, and the reflection mirror 97 are included in the bent shape detection/calculation device 71.

Instead of the optical fiber 83a, a linear member whose electric characteristics are changed by being bent may be disposed. Also, instead of the optical fiber 83a, at least one strain gauge or gyro sensor may be disposed along the longitudinal direction of the insertion unit 20.

In the present embodiment, as described above, the bendable portion 23 is bent up and down, left and right, but may be bent up and down only or left and right only. In such a case, the bent shape detection/calculation device 71 detects the bent shape when the bendable portion 23 is bent in the up and down direction or when the bendable portion 23 is bent in the left and right direction.

Thus, the bending operation amount detection/calculation device 61 detects at least one of the bent shapes when the bendable portion 23 is bent in the up and down direction and the bent shape when the bendable portion 23 is bent in the left and right direction to calculate bent shape information.

Figure 4A:
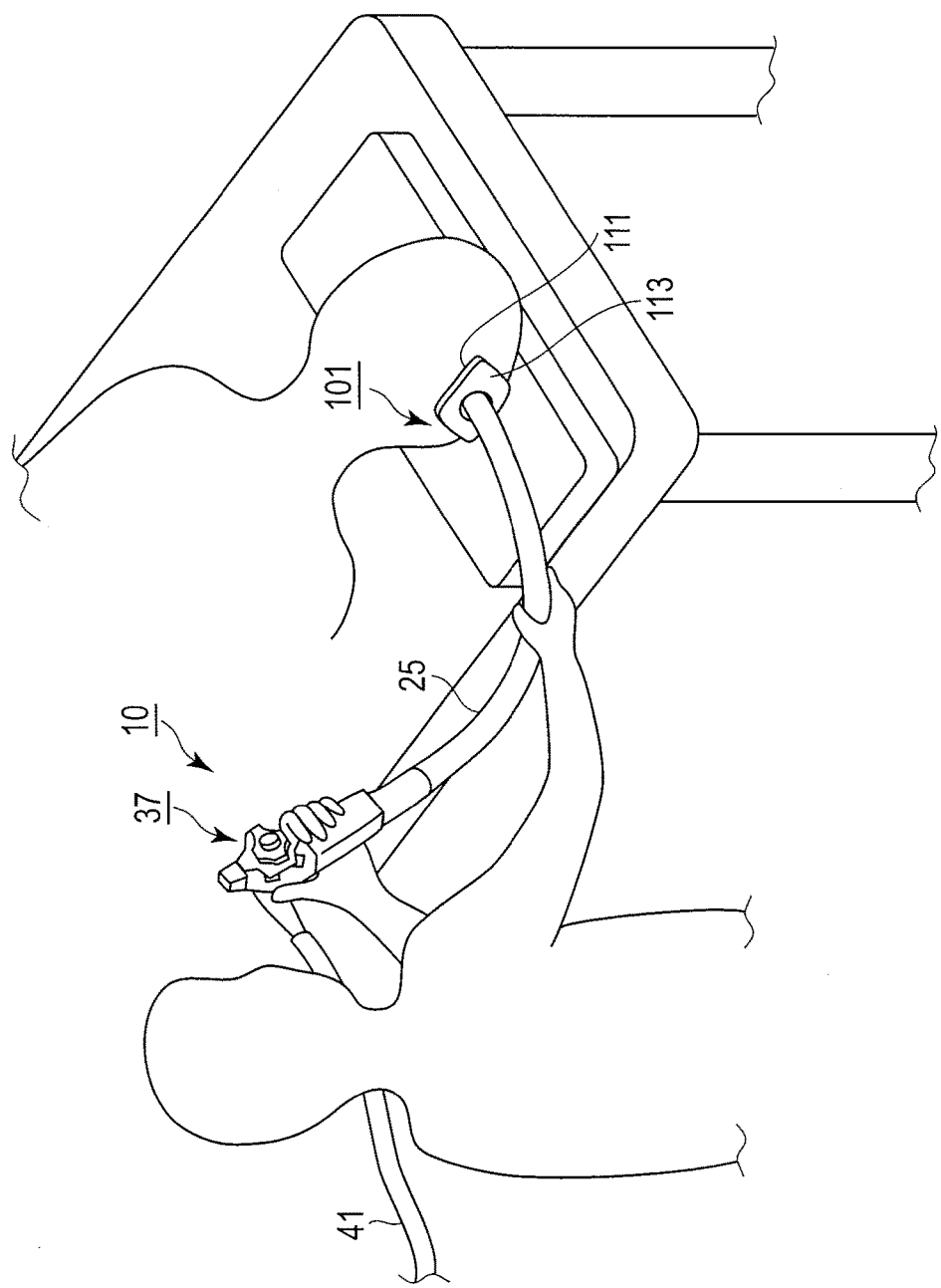
FIG. 4A is a diagram showing a state in which an insertion unit is inserted into a body cavity through an insertion assistant tool.

As shown in FIGS. 4A, 4B, and 4C, the endoscope system 10 further includes an insertion/removal and rotating operation detection/calculation device 101 that detects at least one of an insertion operation of the insertion unit 20 and a rotating operation of the insertion unit 20 to calculate insertion/removal and rotation information indicating at least one of the detected insertion operation and rotating operation.

The insertion/removal and rotation information includes at least one of insertion/removal information and rotation information. The insertion/removal information includes at least one of, for example, the insertion/removal amount of the insertion unit 20 and information obtained by differentiating the insertion/removal amount with respect to time at least once. The differentiated information is, for example, an insertion/removal speed. The rotation information includes at least one of, for example, the rotation amount including the rotating direction of the insertion unit 20 and information obtained by differentiating the rotation amount with respect to time at least once. The differentiated information is, for example, a rotation speed. When the insertion/removal and rotating operation detection/calculation device 101 calculates the insertion/removal and rotation information or when the insertion unit 20 is inserted into a body cavity through an opening portion 111 like, for example, a mouth, as shown in FIG. 4A, an insertion assistant tool 113 is disposed in the opening portion 111. The insertion assistant tool 113 assists the insertion to insert the insertion unit 20 into a body cavity. Thus, the insertion unit 20 is inserted into the body cavity through the opening portion 111 via the insertion assistant tool 113. The insertion assistant tool 113 is, for example, a mouth piece.

As shown in FIG. 4B, the insertion/removal and rotating operation detection/calculation device 101 includes an insertion/removal detection unit 103 that detects the insertion/removal of the insertion unit 20 including the bendable portion 23 and an insertion/removal calculation unit 105 that calculates the insertion/removal amount and insertion/removal speed based on detection results by the insertion/removal detection unit 103.

The insertion unit 20 (the flexible tubular portion 25) includes a read portion 107 like, for example, a grid pattern disposed on the outer circumferential surface of the insertion unit 20 (the flexible tubular portion 25) so that the insertion/removal detection unit 103 can detect the insertion/removal of the insertion unit 20. The read portion 107 moves together with the insertion unit 20 when the insertion unit 20 moves forward or backward for insertion/removal.

The insertion/removal detection unit 103 reads the read portion 107 moving together with the insertion unit 20 to detect the movement of the read portion 107. Accordingly, the insertion/removal detection unit 103 detects the insertion/removal of the insertion unit 20. The insertion/removal detection unit 103 is, for example, an encoder. The insertion/removal detection unit 103 is disposed in the insertion assistant tool 113 disposed in the opening portion 111 when the insertion unit 20 is inserted into a body cavity via the opening portion 111.

The insertion/removal calculation unit 105 calculates the insertion/removal amount (the insertion amount or removal amount) and the insertion/removal speed (the insertion speed or removal speed) of the insertion unit 20 (the bendable portion 23) based on detection results detected by the insertion/removal detection unit 103. As shown in FIGS. 1 and 4B, the insertion/removal calculation unit 105 is disposed, for example, in the control apparatus 19.

The insertion/removal and rotating operation detection/calculation device 101 further includes a rotation detection unit 123 that detects a rotation of the insertion unit 20 including the bendable portion 23 and a rotation calculation unit 125 that calculates the rotation amount and rotation speed based on detection results by the rotation detection unit 123.

The rotation indicates movement in the circumferential direction of the insertion unit 20 with respect to the axial direction of the insertion unit 20 and indicates rotation (rotational movement) of the insertion unit 20.

The rotation detection unit 123 reads the read portion 107 rotating together with the insertion unit 20 to detect the rotation of the read portion 107. Accordingly, the rotation detection unit 123 detects a rotation of the insertion unit 20. The rotation detection unit 123 is, for example, an encoder. Like the insertion/removal detection unit 103, the rotation detection unit 123 is disposed in the insertion assistant tool 113. The rotation detection unit 123 may be integrated with or separated from the insertion/removal detection unit 103.

The rotation calculation unit 125 calculates the rotation amount including the rotating direction and the rotation speed of the insertion unit 20 (the bendable portion 23) based on detection results by the rotation detection unit 123. As shown in FIGS. 1 and 4B, the rotation calculation unit 125 is disposed, for example, in the control apparatus 19.

As shown in FIG. 4C, instead of the read portion 107, an insertion rotator 129 that is in contact with the outer circumferential surface of the insertion unit 20 and rotates when the insertion unit 20 is inserted and a rotation rotator 131 that is in contact with the outer circumferential surface of the insertion unit 20 and rotates when the insertion unit 20 is rotated may be disposed.

The insertion rotator 129 and the rotation rotator 131 are, for example, rollers that are disposed in the insertion assistant tool 113 whose illustration is omitted in FIG. 4C, in contact with the outer circumferential surface of the insertion unit 20, and rotated by insertion or rotation of the insertion unit 20. The read portion 107 described above is disposed on the outer circumferential surface of the insertion rotator 129 and the outer circumferential surface of the rotation rotator 131. The insertion/removal detection unit 103 reads the read portion 107 rotating together with the insertion rotator 129 to detect the rotation of the read portion 107. Accordingly, the insertion/removal detection unit 103 detects the insertion/removal of the insertion unit 20. The rotation detection unit 123 reads the read portion 107 rotating together with the rotation rotator 131 to detect the rotation of the read portion 107. Accordingly, the rotation detection unit 123 detects a rotation of the insertion unit 20.

The insertion/removal calculation unit 105 calculates the amount of rotation of the insertion rotator 129, that is, the insertion/removal amount (the insertion amount or removal amount) and the insertion/removal speed (the insertion speed or removal speed) of the insertion unit 20 (the bendable portion 23) based on detection results detected by the insertion/removal detection unit 103. Also, the rotation calculation unit 125 calculates the amount of rotation of the rotation rotator 131, that is, the rotation amount and the rotation speed of the insertion unit 20 (the bendable portion 23) based on detection results by the rotation detection unit 123.

The insertion/removal and rotation information only needs to include at least one of the insertion/removal amount, insertion/removal speed, rotation amount containing the rotating direction, and rotation speed of the insertion unit 20 and thus, the insertion/removal and rotating operation detection/calculation device 101 only needs to include at least one of an insertion/removal device including the insertion/removal detection unit 103 and the insertion/removal calculation unit 105 and an insertion/removal device including the rotation detection unit 123 and the rotation calculation unit 125.

Figure 5:
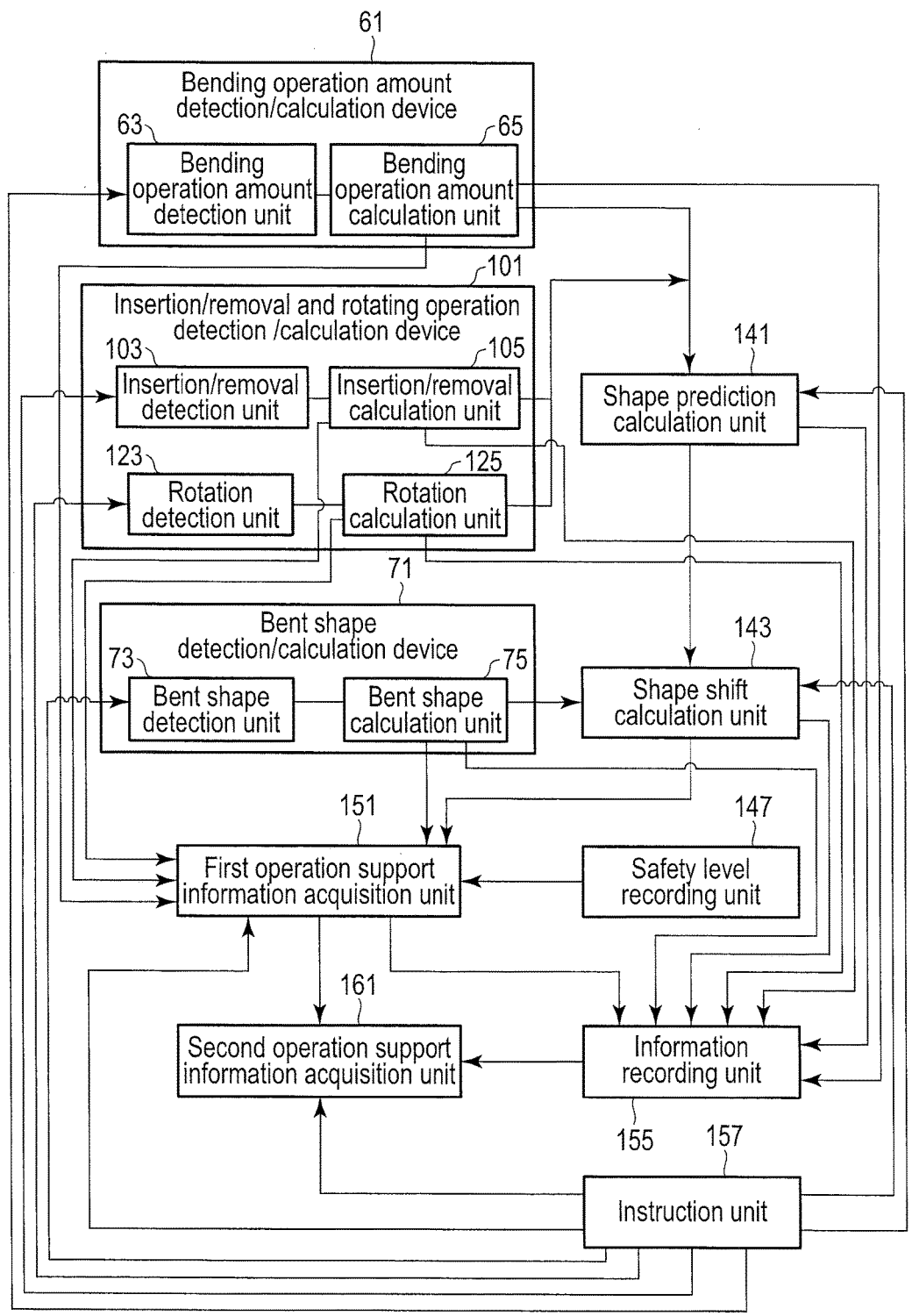
FIG. 5 is a diagram illustrating a control system of an endoscope system.

As shown in FIG. 5, the endoscope system 10 includes a shape prediction calculation unit 141 that predicts (estimates) the bent shape of the bendable portion 23 corresponding to the bending operation amount to calculation prediction information showing a prediction based on calculation results (bending operation amount information) calculated by the bending operation amount detection/calculation device 61 (the bending operation amount calculation unit 65). The shape prediction calculation unit 141 predicts how much the bendable portion 23 is bent by an operation of the bending operation unit 37, that is, the bent shape (state) of the bendable portion 23 bent by an operation of the bending operation unit 37 when no external force acts on the insertion unit 20.

The shape prediction calculation unit 141 may calculate prediction information by further adding calculate results calculated by the insertion/removal and rotating operation detection/calculation device 101 to the bending operation amount information. The calculate result shows insertion/removal and rotation information and shows at least one of the insertion/removal amount, insertion/removal speed, rotation amount, and rotation speed.

As shown in FIG. 1, the shape prediction calculation unit 141 is disposed, for example, in the control apparatus 19.

As shown in FIG. 5, the endoscope system 10 also includes a shape shift calculation unit 143 that calculates shift information based on calculation results (bent shape information) calculated by the bent shape detection/calculation device 71 (the bent shape calculation unit 75) and calculation results (prediction information) calculated by the shape prediction calculation unit 141. The shift information indicates at least one of shift amounts and shift changes over time. The shift amount is a difference between the bent shape of the bendable portion 23 that is actually bent and the bent shape of the bendable portion 23 predicted based on bending operation amount information, that is, a difference between the actual value and a predicted value. The shift change over time indicates at least one of information obtained by integrating a shift amount with respect to time at least once and information obtained by differentiating a shift amount with respect to time at least once. As shown in FIG. 1, the shape shift calculation unit 143 is disposed, for example, in the control apparatus 19.

As shown in FIG. 5, the endoscope system 10 also includes a safety level recording unit 147 that records the judgment of safety of operating the bendable portion 23, that is, the safety level that indicates the safety standard of operation.

The operation indicates at least one of, for example, an operation of the bending operation mechanism 39, insertion/removal of the insertion unit 20, and a rotation of the insertion unit 20 to bend the bendable portion 23.

The safety level indicates a shift information safety level corresponding to shift information, a bending operation amount information safety level corresponding to a bending operation amount (bending operation amount information), a bent shape information safety level corresponding to bent shape information, and an insertion/removal and rotation information safety level corresponding to insertion/removal and rotation information.

More specifically, the safety level indicates the allowable range of shift amount, the allowable range of shift changes over time (time integral, time differential), the maximum value of bending operation amount, the maximum value of bent shape, the maximum value of insertion/removal amount of the insertion unit 20, the maximum value when the insertion/removal amount is differentiated with respect to time at least once (the insertion/removal speed of the insertion unit 20), the maximum value of rotation amount of the insertion unit 20, and the maximum value when the rotation amount is differentiated with respect to time at least once (the rotation speed of the insertion unit 20).

The shift information, bending operation amount information, bent shape information, and insertion/removal and rotation information are parameters necessary for first operation support information instructed by, for example, an instruction unit 157 described later, the shift information, bending operation amount information, bent shape information, and insertion/removal and rotation information are information group which is selected target as first operation support information, that is, a selected target information group.

The shift information safety level, bending operation amount information safety level, bent shape information safety level, and insertion/removal and rotation information safety level form a safety level group corresponding to the selected target information group.

The safety level recording unit 147 may record only safety levels of parameters (for example, the shift amount only) necessary for first operation support information instructed by, for example, the instruction unit 157 described later.

As shown in FIG. 1, the safety level recording unit 147 is disposed, for example, in the control apparatus 19.

Also, as shown in FIG. 5, the endoscope system 10 includes a first operation support information acquisition unit 151 that acquires first operation support information indicating information to support an operation based on at least one of calculation results (bending operation amount information) calculated by the bending operation amount calculation unit 65 and calculation results (bent shape information) calculated by the bent shape calculation unit 75.

More specifically, the first operation support information acquisition unit 151 acquires first operation support information by combining and calculating bent shape information and prediction information.

Still more specifically, the first operation support information acquisition unit 151 acquires shift information from the shape shift calculation unit 143 to acquire first operation support information corresponding to the shift information.

When the first operation support information acquisition unit 151 acquires first operation support information corresponding to the shift information, the first operation support information acquisition unit 151 acquires first operation support information corresponding to the shift information based on at least one piece of information contained in the shift information and the shift information safety level corresponding to the information. More specifically, the first operation support information acquisition unit 151 acquires first operation support information corresponding to shift information indicating a shift amount based on the shift amount and shift amount safety level. Also, the first operation support information acquisition unit 151 acquires first operation support information corresponding to shift information indicating shift changes over time based on shift changes over time and the safety level of shift changes over time. The first operation support information acquisition unit 151 may acquire both of first operation support information corresponding to shift information indicating a shift amount and first operation support information corresponding to shift information indicating shift changes over time.

In this case, the first operation support information is an index showing the ratio of a shift amount to the shift amount safety level (allowable range) and shows the degree of safety of the shift amount. The first operation support information is also an index showing the ratio of shift changes over time to the safety level of shift changes over time and shows the degree of safety of shift changes over time. Thus, the first operation support information is an index showing the ratio of shift information to the shift information safety level.

As shown in FIG. 1, the first operation support information acquisition unit 151 is disposed, for example, in the control apparatus 19.

Incidentally, the first operation support information acquisition unit 151 may acquire first operation support information corresponding to bending operation amount information, bent shape information, and insertion/removal and rotation information.

When the first operation support information acquisition unit 151 acquires first operation support information corresponding to bending operation amount information, the first operation support information acquisition unit 151 acquires first operation support information corresponding to bending operation amount information based on bending operation amount information in the bending operation amount detection/calculation device 61 and the bending operation amount information safety level in the safety level recording unit 147.

In this case, the first operation support information is an index showing the ratio of the bending operation amount (bending operation amount information) to the bending operation amount information safety level (maximum value of the bending operation amount) and shows the degree of safety of bending operation amount (bending operation amount information) changes over time.

When the first operation support information acquisition unit 151 acquires first operation support information corresponding to bent shape information, the first operation support information acquisition unit 151 acquires first operation support information corresponding to bent shape information based on bent shape information and the bent shape information safety level (maximum value of the bent shape) in the safety level recording unit 147.

In this case, the first operation support information is an index showing the ratio of the bent shape information to the bent shape information safety level (maximum value of the bent shape) and shows the degree of safety the bent shape information.

When the first operation support information acquisition unit 151 acquires first operation support information corresponding to insertion/removal and rotation information, the first operation support information acquisition unit 151 acquires first operation support information corresponding to insertion/removal and rotation information based on insertion/removal and rotation information in the insertion/removal and rotating operation detection/calculation device 101 and the insertion/removal and rotation information safety level in the safety level recording unit 147.

In this case, the first operation support information is an index showing the ratio of insertion/removal and rotation information to the insertion/removal and rotation information safety level and shows the degree of safety of, for example, the insertion/removal amount, time differential of the insertion/removal amount (insertion/removal speed), rotation amount, and time differential of the rotation amount (rotation speed).

Such a first operation acquisition unit acquires at least one of first operation support information corresponding to a shift amounts, first operation support information corresponding to shift changes over time, first operation support information corresponding to bending operation amount information, first operation support information corresponding to bent shape information, first operation support information corresponding to an insertion/removal amount, first operation support information corresponding to an insertion/removal speed, first operation support information corresponding to a rotation amount, and first operation support information corresponding to a rotation speed.

That is, the first operation support information acquisition unit 151 acquires at least one piece of first operation support information corresponding to each piece of information of a selected target information group based on a safety level group corresponding to the selected target information group.

However, the first operation support information acquisition unit 151 need not acquire all first operation support information described above and may acquire, for example, only first operation support information of parameters (for example, the shift amount only) instructed by the instruction unit 157 described later.

For example, the first operation support information becomes an index of at least one parameter described above (for example, the shift amount only).

Also, as shown in FIG. 5, the endoscope system 10 includes an information recording unit 155 that records at least one of the shift amount, shift changes over time, bending operation amount information, bent shape information, insertion/removal amount, insertion/removal speed, rotation amount, rotation speed, prediction information, and first operation support information, more specifically, parameters such as the shift amount necessary for first operation support information. The information recording unit 155 may record only parameters necessary for first operation support information instructed by, for example, the instruction unit 157 described later in predetermined timing instructed by, for example, the instruction unit 157. As shown in FIG. 1, the information recording unit 155 is disposed, for example, in the control apparatus 19.

Also, as shown in FIG. 5, the endoscope system 10 includes the instruction unit 157 that instructs to perform at least one of an calculation of bending operation amount information in the bending operation amount detection/calculation device 61, an calculation of bent shape information in the bent shape detection/calculation device 71, an calculation of insertion/removal and rotation information in the insertion/removal and rotating operation detection/calculation device 101, an calculation of prediction information in the shape prediction calculation unit 141, an calculation of shift information in the shape shift calculation unit 143, an calculation of first operation support information in the first operation support information acquisition unit 151, a recording by the information recording unit 155, and an calculation of second operation support information in a second operation support information acquisition unit 161 described later in predetermined timing. As shown in FIG. 1, the instruction unit 157 is disposed, for example, in the control apparatus 19.

Also, as shown in FIG. 5, the endoscope system 10 includes the second operation support information acquisition unit 161 that, when at least one of indexes corresponding to the shift amount, shift changes over time, bending operation amount information, bent shape information, insertion/removal amount, insertion/removal speed, rotation amount, and rotation speed can be determined to exceed the respective safety level from the index in first operation support information (index) acquired by the first operation support information acquisition unit 151, acquires second operation support information that indicates to guide the index to the respective safety level so that the index is within the range of the respective safety level.

The second operation support information acquisition unit 161 acquires second operation support information based on first operation support information acquired by the first operation support information acquisition unit 151. Thus, if the first operation support information acquisition unit 151 acquires only first operation support information corresponding to the shift amount, the second operation support information acquisition unit 161 acquires only second operation support information corresponding to the shift amount based on the first operation support information. In this case, the second support information is information indicating that the shift amount is guided to the shift amount safety level so that the shift amount is within the range of the shift amount safety level.

When a deviation of a parameter from the safety level is predicted based on the parameter recorded in the information recording unit 155, the second operation support information contains the amount or direction so that the parameter falls within the range of the safety level. That is, when a deviation of the shift amount, shift changes over time, bending operation amount information, bent shape information, insertion/removal amount, insertion/removal speed, rotation amount, or rotation speed from the respective safety level is predicted based on parameters such as the shift amount acquired by the information recording unit 155 in predetermined timing, the second operation support information is information indicating that an operation is rolled back.

The monitor 16 described above displays at least one of bending operation amount information, bent shape information, insertion/removal and rotation information, prediction information, shift information, first operation support information, and second operation support information.

Next, an operation method in the present embodiment will be described.

As shown in FIG. 4A, the insertion assistant tool 113 is disposed in the opening portion 111 and the insertion unit 20 is inserted into a body cavity via the insertion assistant tool 113.

At this point, the insertion/removal and rotating operation detection/calculation device 101 calculates insertion/removal and rotation information containing at least one of the insertion/removal amount, insertion/removal speed, rotation amount, and rotation speed of the insertion unit 20.

The bending operation unit 37 is operated to bend the bendable portion 23. At this point, the bending operation amount detection/calculation device 61 calculates bending operation amount information.

Also, the bent shape detection/calculation device 71 calculates bent shape information.

Next, the shape prediction calculation unit 141 predicts (estimates) the bent shape of the bendable portion 23 corresponding to the bending operation amount based on bending operation amount information to calculate prediction information. At this point, the shape prediction calculation unit 141 may calculates prediction information by further adding insertion/removal and rotation information to bending operation amount information.

The shape shift calculation unit 143 calculates shift information based on bent shape information and prediction information.

Various calculations described above are performed in predetermined timing under instructions from the instruction unit 157.

The first operation support information acquisition unit 151 acquires shift information indicating at least one of the shift amount and shift changes over time from the shape shift calculation unit 143 and acquires the shift amount safety level or safety level of shift changes over time from the safety level recording unit 147. Then, the first operation support information acquisition unit 151 acquires, for example, first operation support information corresponding to the shift information indicating a shift amount based on the shift amount and the shift amount safety level or acquires first operation support information corresponding to the shift information indicating shift changes over time based on the shift changes over time and the safety level of shift changes over time. The first operation support information is an index showing the ratio of the shift amount to the shift amount safety level (allowable range) or an index showing the ratio of shift changes over time to the safety level of shift changes over time.

Also, the first operation support information acquisition unit 151 acquires bending operation amount information from the bending operation amount detection/calculation device 61 and the bending operation amount information safety level from the safety level recording unit 147. Then, the first operation support information acquisition unit 151 acquires first operation support information corresponding to the bending operation amount information based on the bending operation amount information and the bending operation amount information safety level. In this case, the first operation support information is an index showing the ratio of the bending operation amount (bending operation amount information) to the bending operation amount information safety level (maximum value of the bending operation amount).

Also, the first operation support information acquisition unit 151 acquires bent shape information from the bent shape detection/calculation device 71 and the bent shape information safety level from the safety level recording unit 147. Then, the first operation support information acquisition unit 151 acquires first operation support information corresponding to the bent shape information based on the bent shape information and the bent shape information safety level. In this case, the first operation support information is an index showing the ratio of the bent shape information to the bent shape information safety level (maximum value of the bent shape).

Also, the first operation support information acquisition unit 151 acquires insertion/removal and rotation information from the insertion/removal and rotating operation detection/calculation device 101. Also, the first operation support information acquisition unit 151 acquires the insertion/removal and rotation information safety level from the safety level recording unit 147. Then, the first operation support information acquisition unit 151 acquires first operation support information corresponding to the insertion/removal and rotation information based on the insertion/removal and rotation information and the safety level of insertion/removal and rotation information. In this case, the first operation support information is an index showing the ratio of the insertion/removal and rotation information to the safety level thereof.

However, the first operation support information acquisition unit 151 need not acquire all first operation support information described above and may acquire only first operation support information of parameters (for example, the shift amount only) instructed by the instruction unit 157.

Thus, the first operation support information acquisition unit 151 may acquire at least one of first operation support information corresponding to shift information, first operation support information corresponding to bending operation amount information, first operation support information corresponding to bent shape information, and first operation support information corresponding to insertion/removal and rotation information. When a plurality of pieces of first operation support information is calculated, the first operation support information acquisition unit 151 may combine the plurality of pieces of information.

Next, the information recording unit 155 records at least one of the shift amount, shift changes over time, bending operation amount information, bent shape information, insertion/removal and rotation information, prediction information, and first operation support information, which is each of the above indexes, more specifically, information necessary for the first operation support information in predetermined timing.

Next, the second operation support information acquisition unit 161 acquires second operation support information based on first operation support information acquired by the first operation support information acquisition unit 151. The second operation support information indicates an amount that, when, for example, the insertion/removal amount exceeds the insertion/removal and rotation information safety level, allows the insertion/removal amount to fall within the range of the insertion/removal and rotation information safety level. The amount is an amount that cancels out an operation of insertion/removal or indicates that an operation of insertion/removal is rolled back.

The monitor 16 displays at least one of bending operation amount information, insertion/removal and rotation information, bent shape information, first operation support information, second operation support information, prediction information, and shift information.

As described above, various operations are performed in predetermined timing like simultaneously or individually under instructions of the instruction unit 157.

Thus, according to the present embodiment, first operation support information can directly be acquired by the first operation support information acquisition unit 151 easily with high precision based on at least one of bending operation amount information and bent shape information, more specifically, bending operation amount information (bending operation amount of the bending operation mechanism 39 to bend the bendable portion 23), bent shape information (bent shape of the bendable portion 23 that is actually bent), and shift information (when bending operation amount information and bent shape information are used).

Also, according to the present embodiment, the pressure-sensitive sensor can be made unnecessary by using bending operation amount information and bent shape information so that first operation support information can easily be acquired without being aware of optimization or arrangement position of the pressure-sensitive sensor or noise. Also, according to the present embodiment, the pressure-sensitive sensor can be made unnecessary and so the distal end portion of the insertion unit 20 can be made thin. Also, according to the present embodiment, first operation support information of various parameters can simultaneously be detected.

Also, according to the present embodiment, only the optical fibers 83a, 83b are disposed inside the insertion unit 20 to acquire first operation support information and devices other than the optical fibers 83a, 83b such as the shape prediction calculation unit 141 and the shape shift calculation unit 143 are disposed in the operation unit 30 or the control apparatus 19. Thus, in the present embodiment, highly precise first operation support information can easily be acquired while the insertion unit 20 is made thin.

Also, according to the present embodiment, even if the bendable portion 23 is bent in at least one of the up and down direction and the left and right direction, bending operation amount information can be calculated by the bending operation amount detection/calculation device 61 and bent shape information can be calculated by the bent shape detection/calculation device 71 and, as a result, highly precise first operation support information can easily be acquired by the first operation support information acquisition unit 151.

Also, according to the present embodiment, the shape shift calculation unit 143 can calculate shift information by prediction information being calculated by the shape prediction calculation unit 141 based on bending operation amount information so that highly precise first operation support information can easily be acquired.

Also, according to the present embodiment, the shape prediction calculation unit 141 can calculate more precise prediction information by calculating prediction information after insertion/removal and rotation information being added to bending operation amount information so that highly precise first operation support information can easily be acquired.

Also, according to the present embodiment, shift information can be calculated by the shape shift calculation unit 143 based on bent shape information and prediction information so that highly precise first operation support information can easily be acquired.

Also, according to the present embodiment, first operation support information corresponding to insertion/removal and rotation information can be acquired based on the insertion/removal and rotation information and insertion/removal and rotation information safety level.

Also, according to the present embodiment, the above first operation support information and second operation support information can be acquired by a simple configuration in which the bending operation amount detection unit 63 is disposed in the operation unit 30 and the optical fiber 83 to detect the shape is disposed in the insertion unit 20. Also, according to the present embodiment, the operation unit 30 can be made compact and light thanks to the above arrangement and diverse and highly precise operation support information can be acquired even if the insertion unit 20 is made thin. Thus, according to the present embodiment, the operator can be informed of various kinds of operation support information such as pressure-sensitive information in the distal end portion of the insertion unit 20 and shape information of the insertion unit simultaneously by adopting a very simple and compact configuration. Accordingly, in the present embodiment, a tubular insertion system capable of performing an insertion operation and rotating operation that are safer and easier can be made compact.

Also, according to the present embodiment, only first operation support information of parameters instructed by the instruction unit 157 can be acquired by the instruction unit 157.

Also, according to the present embodiment, more precise first operation support information and second operation support information can be acquired by combining the above first operation support information for each parameter.

Also, according to the present embodiment, the degree of safety of each parameter can easily be judged by using first operation support information as an index showing the ratio of the parameter, for example, the shift amount to the safety level of the parameter.

Also, according to the present embodiment, second operation support information can be acquired based on first operation support information and parameters can be guided so that such parameters are within the range of the safety level based on the second operation support information to be able to ensure safety of the parameters.

Also, according to the present embodiment, information for safe operation can easily be obtained to perform a safe operation by using second operation support information comprising the amount or direction so that a parameter such as the shift amount falls within the range of the safety level.

Also, according to the present embodiment, the monitor 16 displays at least one of bending operation amount information, insertion/removal and rotation information, bent shape information, first operation support information, second operation support information, prediction information, and shift information and thus, the operator can be information of the above information.

The endoscope system (tubular insertion system) 10 according to the present embodiment may also be used for industrial use and in such a case, the insertion unit 20 is inserted into a tube. Thus, the insertion unit 20 may be inserted into a tubular hollow including, for example, a body cavity (lumen) for medical use and also, for example, tubes for industrial use. The endoscope system (tubular insertion system) 10 is not limited to the insertion system 20 and may also be used for forceps of the endoscope 12 or a catheter. The endoscope system 10 is particularly effective for forceps of the endoscope 12 in which an operation mechanism for surgery or work is embedded at the distal end.

The present invention is not limited to the above embodiment unchanged and structural elements thereof may be modified without deviating from the scope thereof in the stage of the working. In addition, various inventions may be formed by appropriately combining a plurality of structural elements disclosed in the above embodiment.

What is claimed is:

1. A tubular insertion system comprising:
an insertion unit including a bendable portion to be bent;
a bending operation mechanism that operates the bendable portion to bend the bendable portion;
a bending operation amount detection/calculation device comprising one or more first sensors that detect an operation of the bending operation mechanism to calculate bending operation amount information indicating an amount of the operation; and
a controller configured to:
detect a bent shape of the bendable portion based on one or more second sensors operatively connected to the bendable portion to calculate bent shape information indicating the bent shape;
determine shift information including a shift amount between the bending operation amount information and the bent shape information;
retrieve one or more levels of safety for an operation of the bendable portion;
acquire first operation support information for determining whether the operation of the bendable portion is within a safety threshold based on the shift amount and the one or more levels of safety, the first operation support information being an index, the index being a ratio of the shift information to an allowable range of the one or more levels of safety; and
display the first operation support information.

2. The tubular insertion system according to claim 1, wherein the controller is further configured to calculate prediction information of the bent shape of the bendable portion corresponding to the amount of the operation based on the bending operation amount information.

3. The tubular insertion system according to claim 2, wherein the controller acquires the first operation support information by combining and calculating the bent shape information and the prediction information of the bent shape.

4. The tubular insertion system according to claim 3, wherein the controller calculates the shift information based on the bent shape information and the prediction information of the bent shape,
when information containing at least one of the shift amount as a difference between the bent shape of the bendable portion and a bent shape of the bendable portion predicted based on the bending operation amount information, information obtained by differentiating the shift amount with respect to time at least once, and information obtained by integrating the shift amount with respect to time at least once is defined as the shift information.

5. The tubular insertion system according to claim 4, wherein the controller acquires the shift information by corresponding the first operation support information to the shift information.

6. The tubular insertion system according to claim 5, wherein the controller acquires the first operation support information corresponding to the shift information based on at least one piece of information contained in the shift information and the one or more levels of safety corresponding to the at least one piece of information contained in the shift information.

7. The tubular insertion system according to claim 2, further comprising: an insertion/removal and rotating operation detection/calculation device comprising one or more sensors that detect at least one of an insertion/removal operation and a rotating operation of the insertion unit to calculate insertion/removal and rotation information indicating at least one of the detected insertion/removal operation and rotating operation.

8. The tubular insertion system according to claim 7, wherein the controller calculates the prediction information of the bent shape by further adding the insertion/removal and rotation information to the bending operation amount information.

* * * * *